United States Patent [19]

Sherba et al.

[11] Patent Number: 5,149,524

[45] Date of Patent: Sep. 22, 1992

[54] ANTIMICROBIAL POLYMERIC QUATERNARY AMMONIUM SALTS

[75] Inventors: Samuel E. Sherba, Willingboro, N.J.; Raj J. Mehta, Gujarat, India; Margaret M. Bowers-Daines; Adam Chi-Tung Hsu, both of Lansdale, Pa.

[73] Assignee: Rohm and Haas Company, Philadelphia, Pa.

[21] Appl. No.: 637,085

[22] Filed: Jan. 3, 1991

[51] Int. Cl.$^5$ .................. A61K 31/74; L08G 75/00
[52] U.S. Cl. .................. 424/78.36; 424/78.38; 424/78.07
[58] Field of Search .................. 528/423, 373; 424/78.36, 78.38

[56] References Cited

U.S. PATENT DOCUMENTS 2,261,002 10/1941 Ritter .................. 260/570
2,271,378 1/1942 Searle .................. 167/22

OTHER PUBLICATIONS

Chem. Abstracts vol. 113 (25) 231141q.
Chem. Abstracts vol. 106 (1) 4890V.
Knorr et al., Ber. 39, 1425 (1906).
Kern et al., J. Prakt Chem 159, 193 (1941).
Carothers, JACS, 2548 (1929).
Marvel et al., JACS, 49,2279 (1927).
Marvel et al. JACS, 52,287 (1930).
Marvel et al., JACS, 55,753 (1933).
Marvel et al., JACS, 56,725 (1934).
Marvel et al., JACS, 57,1127 (1935).
Rembaum et al., Polymer Letters, 6, 159 (1968).
Noguchi et al., Poly Prepr. ACS Dev Polym Chem 10, 718 (1969).
Bortel et al., Makromol Chem, 182,3099–3108 (1981).
Bortel et al., Makromol Chem, 188,2019 (1987).

Primary Examiner—Thurman K. Page
Assistant Examiner—Peter F. Kulkosky
Attorney, Agent, or Firm—Michael B. Fein

[57] ABSTRACT

In one aspect, compounds, methods of using them, compositions comprising such compounds, and uses of such compositions . These objects, and others which will become apparent from the following disclosure, are achieved by the present invention which comprises in one aspect compounds of the formula

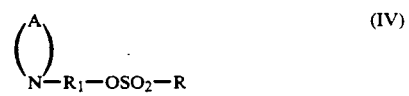

wherein
R is alkyl, cycloakyl, aryl, substituted aryl, alkaryl optionally substituted on the aryl portion, or aralkyl optionally substituted on the aryl portion, R having up to 20 carbon atoms and is optionally branced, and A is $(CH_2)_p$, $(CH_2)_q-O-(CH_2)_r$, or $(CH_2)_q-S-(CH_2)_r$, wherein p=2 to 8, q=1 to 8, and r=1 to 8.

$R_1 = -(CH_2)_m-, -(CH_2CH_2-O)_n-CH_2CH_2-$, or $-(CH_2CH_2CH_2-O)_n-CH_2CH_2CH_2-$.

In another aspect, the invention comprises polymers of the formula

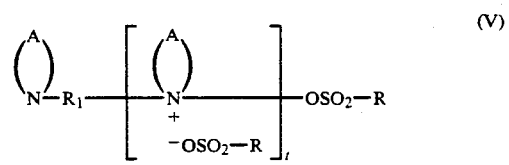

15 Claims, No Drawings

ANTIMICROBIAL POLYMERIC QUATERNARY AMMONIUM SALTS

BACKGROUND OF THE INVENTION

1. Field of the Invention

This invention relates to control of microorganisms.

2. Description of the Prior Art

The self-condensation of various bromoalkylamines has been studied since 1906 starting with bromoethyldimethylamine which reacted with itself to form a cyclic quat with a 6-membered ring, reported by Knorr and Roth, Ber., 39, 1425 (1906).

Kern and Brenneisen, *J. Prakt. Chem.*, 159, 193 (1941), reported another type of linear polyquat using di-tertiary amines to react with di-halides. Both starting materials are readily available.

Carothers, *JACS*, 51, 2548 (1929) suggested a polymeric quat from bromoalkylamines.

Marvel et al., *JACS*, 49, 2299 (1927) suggested intracyclization of bromobutyldimethylamine to form cyclic quats. Other reports by Marvel and colleagues were published in *JACS*, 52, 287 (1930), *JACS*, 55, 753 (1933), *JACS*, 55, 1977 (1933), *JACS*, 56, 725 (1934), and *JACS*, 57, 1127 (1935).

Ritter, U.S. Pat. No. 2,261,002 and Searle et al, U.S. Pat. No. 2,271,378, both assigned to Dupont, disclosed polymeric quats having pesticidal utility (fungicides, insecticides, disinfectants).

Rembaum, et al, *Polymer Letters*, 6, 159 (1968), named both type polyquats as "aliphatic ionenes".

Noguchi, et al, *Poly. Prepr. ACS Dev. Polym. Chem.*, 10, 718 (1969) reviewed cyclic, linear and polymeric ammonium salts.

Bortel et al, published studies on "Chloro-ionenes"; "Chloro-Ionenes with Ether Bonds in the Backbone Chain. Determination of Rate Constants, Orders of Reaction and Molecular Weights," *Makromol. Chem.*, 182, 3099–3108 (1981), and "Chloro-Ionenes from Dichlorides and tertiary diamines," *Makromol. Chem.*, 188, 2019 (1987).

SUMMARY OF THE INVENTION

It is an object of the present invention to provide new compounds for controlling microorganisms.

A further object is to provide methods of making such compounds, methods of using them, compositions comprising such compounds, and uses of such compositions.

These objects, and others which will become apparent from the following disclosure, are achieved by the present invention which comprises in one aspect compounds of the formula

(IV)

wherein
R is alkyl, cycloalkyl, aryl, substituted aryl, alkaryl optionally substituted on the aryl portion or aralkyl optionally substituted on the aryl portion, R having up to 20 carbon atoms and is optionally branched, and A is $(CH_2)_p$, $(CH_2)_q-O-(CH_2)_r$, or $(CH_2)_q-S-(CH_2)_r$, wherein $p=2$ to 8, $q=1$ to 8, and $r=1$ to 8.

$R_1 = -(CH_2)_m-$, $-(CH_2CH_2-O)_n-CH_2CH_2-$, or $-(CH_2CH_2CH_2-O)_n-CH_2CH_2CH_2-$

In another aspect, the invention comprises polymers of the formula

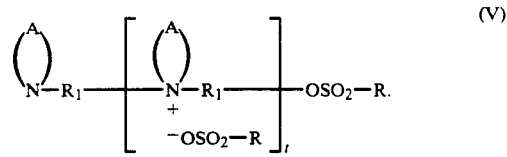

(V)

In another aspect of the invention comprises a process comprising reacting a monoalcohol of the formula $$X-R_1-OH \quad (I)$$

wherein $R_1 = -(CH_2)_m-$, $-(CH_2CH_2-O)_n-CH_2CH_2-$, or $-(CH_2CH_2CH_2-O)_n-CH_2CH_2CH_2-$ in which $m=7$ to 24, $n=1$ to 10, and wherein $X=Br$, Cl, or $OSO_2R$ wherein R is alkyl, cycloalkyl, aryl, substituted aryl, alkaryl optionally substituted on the aryl potion or aralkyl optionally substituted on the aryl portion, R having up to 20 carbon atoms and is optionally branched with a molar excess of secondary ring amine of the formula

(II)

wherein A is $(CH_2)_p$, $(CH_2)_q-O-(CH_2)_r$, or $(CH_2)_q-S-(CH_2)_r$, or $(C_{1-3})$alkyl substituted analogous thereof, wherein $p=2$ to 8, $q=1$ to 8, and $r=1$ to 8 to form a compound of the formula

(III)

and reacting (III) with X'SO2R wherein R is alkyl, cycloalkyl, aryl, substituted aryl, alkaryl optionally substituted on the aryl portion or aralkyl optionally substituted on the aryl portion, R having up to 20 carbon atoms and is optionally branched and wherein X' is Cl or Br, to produce a monomer of the formula

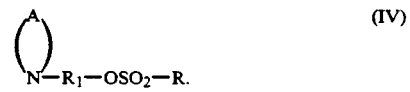

(IV)

A further aspect of the invention is the process comprising polymerizing monomer (IV) to produce a polymer of the formula

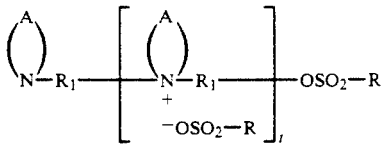

(V)

wherein t=1 to about 100.

A further aspect comprises using a composition comprising the polymer and/or monomer compounds, or the polymer and/or monomer compound itself, to protect a material selected from the group consisting of wood, paint, adhesive, glue, paper, textile, leather, plastics, cardboard, lubricants, cosmetics, food, caulking, feed and industrial cooling water from microorganisms.

DETAILED DESCRIPTION OF THE INVENTION AND THE PREFERRED EMBODIMENT

The compounds of the invention are of formulae IV and V as set forth above. The more preferred embodiments are the polymers of formula V wherein $R_1$ is $-(CH_2)_m-$, m is 11 or 12, R is p-toluene, $A=(CH_2)_p$, wherein p=4, 5, or 6 and t=about 4 to 10.

is preferably piperidine, pyrrolidine, or hexamethyleneimine.

The polymer and monomer compounds are useful for controlling plant pathogenic microbes with low toxicity to said plant. This controlling is achieved by applying the polymers of formula V or compositions comprising the polymers to a plant which is subject to pathogenic microbes. An especially effective use is when the plant pathogen being controlled is of the genus xanthomonas.

The polymers of formula V can also be used in topical sprays along with an adjuvant, for example EDTA or sodium dodecyl alcohol.

As stated above, compositions comprising a polymer according to formula V and either an agronomically acceptable carrier, a cosmetic agent, a cutting oil, a soap or synthetic detergent, a stabilizer, a film forming material, or the like, have a wide range of utility for protecting against or controlling microorganisms from a wide variety of classes including fungus, bacteria, algae, viruses and yeasts. The preferred utilities of the compositions are to protect wood, paint, adhesive, glue, paper, textile, leather, plastics, cardboard, lubricants, cosmetics, food, caulking, feed and industrial cooling water from microorganisms.

We discovered that the polymers of the invention are very active. The polymers, contrary to related commercial quat biocides, do not lose activity in the presence of organic matter; they are non-corrosive to metals and are non-foaming.

The following lists specific industries and applications of the compounds or compositions:

| Industry | Application |
| --- | --- |
| Adhesives, sealants | adhesives |
| | caulks |
| | sealants |
| Agriculture/food chain | adjuvant preservation |
| | agricultural active ingredient |
| | agricultural chemical preservative |
| | agricultural formulations preservation |
| | animal feed preservation |
| | dairy chemicals |
| | fertilizer preservation |
| | food preservation |
| | food processing chemicals |
| | grain preservation |
| | post-harvest produce protection |
| | sugar processing |
| | tobacco |
| Construction products | asphalt/concrete |
| | cement modifiers |
| | construction products |
| | roof mastics |
| | synthetic stucco |
| | wall mastics |
| | joint cement |
| Cosmetics and toiletries | cosmetics |
| | raw materials for cosmetics, toiletries |
| | toiletries |
| Disinfectants, antiseptics | antiseptic |
| | disinfectant |
| Emulsions, dispersions | aqueous dispersions |
| | dispersed pigments |
| | latex |
| | photographic emulsions |
| | pigment slurries |
| | polymer latices |
| Formulated household products | fabric softeners |
| | polishes |
| | waxes |
| | hand dish detergents |
| | raw materials |
| | liquid detergents |
| | hand soaps |
| Industrial processing, misc | electrodeposition paint, baths, rinses. |

| Industry | Application |
|---|---|
| | electrodeposition pre-treatment, post rinses |
| | industrial fluids preservation |
| | pasteurization baths |
| | process aid preservation |
| Industrial water treatment | air washers |
| | cooling towers |
| | cooling water |
| | water cooling |
| | preservation/treatment of wooden cooling tower slats and structural members |
| | can warmers |
| | brewery pasteurization |
| | closed loop water cooling systems |
| Laundry | household laundry products |
| | laundered goods |
| | laundry rinse water |
| | sanitizers-laundry |
| Leather, leather products | leather and hide |
| | leather and hide products |
| Lubricants, hydraulic aids | automotive lubricants and fluids |
| | conveyor lubricants |
| | greases |
| | hydraulic fluids |
| | lubricants |
| Medical devices | diagnostic enzymes |
| | diagnostic kits |
| | medical devices |
| Metalworking & related app's | cutting fluids |
| | metal cleaning |
| | metalworking fluids |
| Odor control (active ingredient) | air conditioning |
| | animal bedding |
| | cat litter |
| | chemical toilet prep'ns |
| | deodorizers |
| | humidifiers |
| | industrial deodorants |
| | sanitary formulations |
| | toilet bowls |
| Paints and coatings coating | emulsions |
| | paints |
| Paper and wood pulp, their products | absorbant materials of paper and wood pulp |
| | packaging materials of paper and wood pulp |
| | paper |
| | paper products |
| | paper treatment |
| | soap wrap |
| | wood pulp |
| | wood pulp products |
| Paper mill | paper mill slimicides |
| | pulp and paper slurries |
| Petroleum refining, fuels | aviation fuels (jet fuel, aviation gas) |
| | crude oils |
| | burner, diesel and turbine fuel oils |
| | coal slurries |
| | diesel fuel additives |
| | diesel fuels |
| | fuels |
| | gasoline |
| | heating oils |
| | hydrocarbons |
| | kerosene |
| | liquefied petroleum gas |
| | petrochemical feedstocks |
| | petroleum products, storage, transportation and production |
| | recycled petroleum products |
| | residual fuel oils |
| | turbine oils |
| Photographic chemicals and process | photographic processing - wash water, rinses |
| | photoprocessing |
| | photoplate processing chemicals (developers, stabilizers etc) |
| Printing | fountain solutions (printing) |
| | ink components (pigments, resins, solvents, etc) |

-continued

| Industry | Application |
|---|---|
| | inks |
| Sanitizers (active) | sanitizers |
| | sanitizers-diary |
| | sanitizers-dental |
| | sanitizers-fermentation |
| | sanitizers-food preparation |
| | sanitizers-food processing |
| | sanitizers-medical |
| | sanitizers-rendering |
| | sanitizers-veterinary |
| Soaps, detergents, cleaners | cleaners |
| | detergents |
| | household cleaners |
| | industrial cleaners |
| | liquid soaps |
| | oil and grease remover |
| | powdered soaps |
| | raw materials for cleaning products |
| | soaps |
| | surfactants |
| Textiles, textile products | bonded fabrics |
| | burlap |
| | canvas |
| | canvas goods |
| | carpet backing |
| | carpets |
| | clothing |
| | coated fabrics |
| | curtains |
| | draperies |
| | engineering textiles |
| | fibers |
| | geotextiles |
| | goods made of textiles |
| | knitted fabrics |
| | nets |
| | nonwoven fabrics |
| | rope |
| | rugs |
| | textile accessories |
| | textile products |
| | textiles |
| | upholstery |
| | woven fabrics |
| | yarn |
| Textile processing | dye fixatives |
| | dyes |
| | fiber lubricants |
| | hand modifiers |
| | sizes |
| | textile processing fluids |
| Therapeutic (active or preservative) | animal health/veterinary |
| | aquaculture |
| | dental |
| | human health |
| | pharmaceutical/therapeutic |
| Water purification | charcoal beds |
| | deionization resins |
| | filters |
| | membranes |
| | reverse osmosis membranes |
| | ultrafilters |
| | water purification |
| | water purification pipes, tubing |
| Wood applications | lazures (wood stains) |
| | wood |
| | wood products |
| Miscellaneous | alcohols |
| | bedding incorporating water or gels |
| | ceramic |
| | contact lens cases-leaching |
| | electronic circuitry |
| | electronics chemicals |
| | enzymes-food production |
| | enzymes |
| | enzymes-industrial |
| | gel cushions |
| | marine antifoulants |
| | mildewcides |
| | wood |
| | plastics |

| Industry | Application |
| --- | --- |
| | laundry |
| | mining |
| | natural rubber latex |
| | oil field injection waters including enhanced recover injection fluids, drilling, fracturing and completion fluids |
| | pipes |
| | plastics |
| | polymer systems |
| | polymers and resins (synthetic and natural) |
| | reagent preservation |
| | rubber |
| | rubber products |
| | skin remover |
| | solid protective/decorative films |
| | stains |
| | swimming pools |
| | waste treatment |
| | water beds |

The amounts of the compound to be used depend on the application. The useful amounts for a particular application are similar to amounts used for other microbicide compounds.

The compound can be used in combination with other microbicides. The term "microbicide" is considered equivalent to "antimicrobial" as used herein.

Suitable methods of application of compounds of formula I to control fungi, bacteria, algae, viruses, yeasts, and the like are in amounts and with carriers, etc., as well known in the art.

The following examples are presented to illustrate a few embodiments of the invention. All parts and percentages are by weight unless otherwise indicated.

The following procedures were used to evaluate biological activity:

This test is run on bacteria in synthetic hard water without the benefit of nutrients. A 1.0% slant tube is used to grow Ps.fl. which is washed with four ml of sterile water. This wash is diluted to a density of 60 to 80 NTU.

The above inoculum is diluted with SHW, 1.5 ml inoculum to 100 ml of SHW. This seeded SHW is used to fill the microtiter wells.

1. To 100 ml of sterile Synthetic Hard Water (SHW) add 1.5 ml of inoculum from the 60–80 NTU slant wash and mix well.

2. Using an 8 channel micro pipet, transfer 100 μl of the mix from a single reservoir tray to each well of the microtiter plate. Add an additional 90 μl to the first row of wells, bringing the total in row 1 to 190 μl.

3. To the top well in each column add 10 μl of compound prep, so that 6 compounds, a blank, and a standard are located along the A row. The 10 μl of 5,000 ppm prep plus 190 μl of Ps.fl. SHW make a compound concentration 250 ppm.

4. Using an 8 channel micropipet, mix and transfer 100 μl from each well of row 1 to the next row, making a 1:1 dilution to 125 ppm of the 6 compounds and standard in row 2.

5. Repeat this to make successive 1:1 dilutions to the bottom row.

6. Allow the plate to incubate for 4 hr.

7. Prepare a microtiter plate containing 100 μl TSB in each well. At one hour the Clonemaster to transfer 5 μl from each well of the SHW plate to the TSB plate for recovering living cells.

8. Incubate this recovery plate for 24 hr. at 30° C. before noting the concentration at which each compound killed the cells in the SHW plate, resulting in clear wells or no growth in the corresponding wells of the TSB recovery plate.

Total Kill Test Protocol

1. Grow Psae in triptocase soy broth

2. Put 100 μl/10 ml of 0.85% saline contained in 0.05M N-tris[hydroxymethyl]methyl-2-amino ethanosulfonic acid buffer at pH 7.0.

3. Fill microtiter plates with 100 μl of #2 except top wells—they contain 190 μl of #2.

4. Add 10 μl of test compound at time zero then serial dilute by 2 X.

5. Using a 96 pin (1.5 μl each pin) Dynatech inoculator recover to triptocase soy broth agar plate by touching agar with 96 pins.

6. Incubate at 30° C. for 48 hours.

7. Read the pin spot where no growth occurred. This is the point that total kill occurs with a certain concentration/test compound at a certain time.

Speed of Kill ("SOK") tests were run as follows:

1. Grow Psae or Saur or Sal chlo on triptocase soy broth agar slants.

2. Wash slants with 10 ml 0.85% saline, 0.05 N-tris[-hydroxymethyl]methyl-2-amino ethanosulfonic acid buffer pH 7.0

3. Pour #2 into sterile vial.

4. Vortex #3.

5. Add 10 ml of #4 to sterile 2 oz jar with a stirring bar.

6. Remove 100 ml of #5 to triptocase soy broth for zero time call count.

7. Add test compound at desired concentrations.

8. With time intervals remove adjuvants to 100 ml of sterile triptocase soy broth.

9. Do cell counts of #8 by pour plating in sterile triptocase soy broth agar.

10. Incubate agar plates at 30° C. for 72 hours.

11. Calculate log reduction of viable cells.

Minimum inhibitory concentration (MIC) values were obtained using a broth, two-fold serial dilution test performed as follows:

A stock solution or dispersion of the test compound, typically at a concentration of 1%, is made in a 5:3:2 solvent solution of acetone, methanol, and water. A volume of the stock solution is dispensed into culture media to give an initial starting test concentration of 500 ppm compound.

When the test is ready to be done, each vessel in the dilution series, except the first vessel, contains an equal volume of compound free broth. The first vessel contains twice the volume of broth with the starting concentration of test compound. One half of the broth from the first vessel is transferred to the second vessel. After being mixed, one half the resulting volume is removed from the second vessel and transferred to the third vessel. The entire cycle is repeated sufficiently to give a series of concentrations amounting to 250, 125, 63, 31, 16, 8, and 4, 2, 1, 0.5, 0.25, and 0.12 ppm.

Each vessel is then inoculated with a cell suspension of the appropriate test organism. Bacteria are grown in broth; fungi on agar slants for a time and at a temperature appropriate to the species being tested; and algae are a mixture of green algae and blue-green bacteria grown in a nutrient media. At the end of the growth period, in the case of bacteria, the broth is vortexed to disperse the cells.

In the case of fungi, the spores are harvested by pipetting water onto the slant and dislodging the spores with a sterile loop. The cell/spore suspension is standardized by controlling incubation time, temperature, and the volume of the diluent. The suspension is then used to inoculate the vessels containing the broth compound.

The algae culture contains green algae and blue-green bacteria, and is obtained from a cooling tower in Spring House, Pa. The algae culture is grown in Allen's medium on a rotary shaker under flourescent room lighting. This culture is further diluted with Allen's medium and then added to the test vessel.

The vessels are then incubated at the appropriate temperature. After the incubation, the vessels are examined for growth/no growth. The minimum inhibitory concentration (MIC) is defined as the lowest concentration of compound that results in complete inhibition of growth of the test organism.

The organisms tested to demonstrate biocidal activity include:

Bacteria

*Pseudomonas fluorescens* (PSFL), gram negative
*Pseudomonas aerugenosa* (PSAE), gram negative
*Escherichia coli* (ECOL), gram negative
*Staphylococcus aureus* (SAUR), gram positive

Fungi

*Aspergillus niger* (ANIG)
*Aureobasidium pullulans* (APUL)

EXAMPLE 1

A. Synthesis of 11-(N-piperidyl)undecane-1-(p-toluene)sulfonate

11-Bromoundecanol (11.00 g., 43.79 mmole) was dissolved in 100 ml. of piperidine and heated at reflux temperature for 18 hours. The reaction mixture was allowed to cool and most of the precipitated piperidine hydrobromide was removed by filtration. The excess piperidine is removed by simple distillation and the resultant solid residue is recrystallized from ethanol and water. After drying, 10.78 g. (96.3% yield) of 1-hydroxy-11-(N-piperidyl)undecane was obtained. m.p. 62°-65° C., $^1$H-NMR (200 MHz, CDCl$_3$) $\delta$=1.2–1.7 ppm, m, 24H; 2.10, broad s, 1H; 2.20–2.45, m, 6H; 3.63, t, 2H.

The 1-Hydroxy-11-(N-piperidyl)undecane (10.70 g., 41.89 mmole) was dissolved in 200 ml. of anhydrous methylene chloride. The solution was cooled to 0° C. with an ice bath and then treated with 4-(N,N-dimethylamino)pyridine (5.12 g., 41.91 mmole) followed by p-toluenesulfonyl chloride (7.99 g., 41.91 mmole). The reaction mixture was stirred at 0° C. for 18 hours or until all of the starting material was consumed as determined by thin layer chromatography on silica gel. When complete, the reaction mixture was washed with water, saturated aqueous sodium bicarbonate solution and saturated aqueous sodium chloride solution. The methylene chloride solution was dried over magnesium sulfate, filtered and concentrated under reduced pressure to afford 11-(N-piperidyl)undecane-1-(p-toluene)-sulfonate as a viscous oil (15.81 g., 92.1% yield). $^1$H-NMR (200 MHz., CDCl$_3$) $\delta$=1.10–1.75 ppm, m, 24H; 2.15–2.65, m, 6H; 2.46, s, 3H; 4.01, t, J=6.4 Hz., 2H; 7.35, d, J=8.3 Hz., 2H; 7.80, d, J=8.3 Hz., 2H. $^1$H-NMR (200 MHz., CD$_3$OD) $\delta$=1.10–1.80 ppm, m, 24H; 2.10–2.70, m, 6H; 2.46, s, 3H; 4.01, t, J=6.2 Hz, 2H; 7.44, d, J=8.2 Hz, 2H; 7.78, d, J=8.2 Hz., 2H. IR(neat) 2925, 2880, 2800, 2760, 1610, 1450, 1360, 1175, 1100, 960, 840, 670 cm$^{-1}$.

B. Polymerization of Poly 11-(N-piperidyl)undecane-1-(p-toluene) sulfonate

On standing over a period of 1–4 weeks, the above monomer polymerizes to form the water soluble polymeric quaternary ammonium salt: poly (11-piperidinium undecane p-toluenesulfonate). m.p. 95°–106° C.

C. Biocidal activity of poly (11-(N-piperidyl)undecane-1-(p-toluene) sulfonate) compared to commercially available quatbiocides The poly 11-(N-piperidyl)undecane-1-(p-toluene) sulfonate exhibits unexpected outstanding biocidal efficacy in complex media in the secondary MIC/SOK test (4–16 ppm range). In a side-by-side test against commercially available quat compounds, poly 11-(N-piperidyl)undecane-1-(p-toluene) sulfonate maintained superior efficacy in the complex media (triptocase soy broth). Especially noteworthy is the Total Kill Test data for of the polymer of the invention and the fact that it is not inactivated by the presence of organic media. In none of the commercially available quats is the nitrogen atom part of a ring.

TABLE 1

| | MIC BIOCIDES TEST DATA (ppm) | | | | | | | |
|---|---|---|---|---|---|---|---|---|
| Quat | Total Kill Test | (G−) PSFL | (G−) PSAE | (G−) ECOL | (G+) SAUR | (F) ANIG | (F) APUL | Modified Total Kill |
| Example 1 (Invention) | 4 | 4 | 16 | 8 | 4 | 16 | 4 | 8 |

TABLE 1-continued

| | | MIC BIOCIDES TEST DATA (ppm) | | | | | | |
|---|---|---|---|---|---|---|---|---|
| Quat | Total Kill Test | (G−) PSFL | (G−) PSAE | (G−) ECOL | (G+) SAUR | (F) ANIG | APUL | Modified Total Kill |
| Comparative A | 63 | >250 | 250 | 250 | >250 | 250 | >250 | |
| Comparative B | 16 | 1 | 8 | 8 | 1 | 4 | 8 | |
| Comparative C | 16 | 1 | 63 | 16 | 2 | 4 | 1 | |

Comparative A = Busan 77 ™ poly[oxyethylene (dimethyliminio) ethylene (dimethyliminio) ethylenedichloride
Comparative B = Hyamine 1600 ™ alkyl dimethylbenzyl ammonium chloride
Comparative C = Hyamine 3500 ™ alkyl dimethylbenzyl ammonium chloride
Invention = Poly 11-(N-piperidyl)undecane-1-(p-toluene) sulfonate

EXAMPLE 2

Following the procedure of Examples 1 A and B except using 12-bromododecanol instead of 11-bromoundecanol, polymer 2 was prepared.

EXAMPLE 3

Following the procedure of Examples 1 A and B except using phenylsulfonyl chloride instead of p-toluene sulfonyl chloride, polymer 3 was prepared.

EXAMPLE 4

Following the procedure of Examples 1 A and B except using p-nitrophenyl sulfonyl chloride instead of p-toluene sulfonyl chloride, polymer 4 was prepared.

EXAMPLE 5

Following the procedure of Examples 1 A and B except using methane sulfonyl chloride, monomer 5 in crystalline form according to formula IV was prepared.

EXAMPLE 6

Following the procedure of Examples 1 A and B except using p-chlorophenyl sulfonyl chloride instead of p-toluene sulfonyl chloride, polymer 6 was prepared.

EXAMPLE 7

Following the procedure of Examples 1 A and B except using hexamethylene imine instead of piperidine, polymer 7 was prepared.

EXAMPLE 8

Following the procedure of Examples 1 A and B except using pyrrolidine instead of piperidine, polymer 8 was prepared.

EXAMPLE 9

Following the procedure of Examples 1 A and B except using 12-bromododecanol was used instead of 11-bromoundecanol and hexamethylene imine instead of piperidine, polymer 9 was prepared.

EXAMPLE 10

Following the procedure of Examples 1 A and B except using 12-bromododecanol and pyrrolidine, polymer 10 was prepared.

EXAMPLE 11

Following the procedure of Examples 1 A and B except using 12-bromododecanol, pyrrolidine, and phenylsulfonylchloride, polymer 11 was prepared.

EXAMPLE 12

Following the procedure of Examples 1 A and B except using 12-bromododecanol, hexamethylene imine, and phenylsulfonyl chloride, polymer 12 was prepared.

EXAMPLE 13

Following the procedure of Examples 1 A and B except using morpholine instead of piperdine, polymer 13 was prepared.

EXAMPLE 14

The polymers or monomer of Examples 2 to 13 were tested with the results reported in Table 2.

TABLE 2

| Example | MIC (ppm) | | | | | | Total Kill Test (ppm) 4 hrs Psae | Modified Total Kill Test* 10 min results |
|---|---|---|---|---|---|---|---|---|
| | Psae | Ecol | Saur | Anig | Apul | Chlor | | |
| 2 | 63 | 4 | 4 | 4 | 1 | 0.5 | >250 | 16 |
| 3 | 16 | 8 | 4 | 8 | 4 | <0.12 | −8 | 8 |
| 4 | >250 | >250 | 8 | 32 | 16 | <0.12 | >250 | >500 |
| 5 | >250 | >250 | >250 | 250 | 125 | >250 | >250 | >500 |
| 6 | 16 | 16 | 63 | 16 | 8 | 250 | 8 | 8 |
| 7 | 32 | 16 | 8 | 4 | 0.5 | <0.12 | 16 | 16 |
| 8 | 16 | 8 | 16 | 4 | 0.25 | 0.25 | 16 | 8 |
| 9 | 32 | 8 | 4 | 4 | 0.5 | 0.5 | 125 | 32 |
| 10 | 4 | 4 | 2 | 1 | 1 | 8 | 32 | 8 |
| 11 | 4 | 4 | 2 | 4 | 2 | 2 | 16 | 8 |
| 12 | 63 | 16 | 8 | 16 | 8 | 8 | 250 | 16 |
| 13 | >250 | >250 | 63 | 63 | 16 | — | 16 | — |

*to kill 2.2 × 10$^4$ CFU in 10 min.

EXAMPLE 15

SOK for Examples 1 and 11 were measured with the following results in log/3 min. against Psae, Saur, and Schlo using 100 ppm of test compound.

| | SOK | | |
|---|---|---|---|
| Example | Psae | Saur | Schlo |
| 1 | 4 | 2 | 2 |

-continued

| | SOK | | |
|---|---|---|---|
| Example | Psae | Saur | Schlo |
| 11 | 6 | 4 | 5 |

We claim:

1. Process comprising polymerizing a monomer

$$\left(\begin{array}{c}A\\ \end{array}\right)_{N-R_1-OSO_2-R} \qquad (IV)$$

wherein $R_1 = -(CH_2)_m-$, $-(CH_2CH_2-O)_n-CH_2CH_2-$, or $-(CH_2CH_2CH_2-O)_n-CH_2CH_2CH_2-$ in which $m = 7$ to 24, $n = 1$ to 10;

wherein R is alkyl, cycloalkyl, aryl, substituted aryl, alkaryl optionally substituted on the aryl potion or aralkyl optionally substituted on the aryl portion, R having up to 20 carbon atoms and is optionally branched;

wherein A is $(CH_2)_p$, $(CH_2)_q-O-(CH_2)_r$, or $(CH_2)_q-S-(CH_2)_r$, or $(C_{1-3})$alkyl substituted analogous thereof, wherein $p=2$ to 8, $q=1$ to 8, and $r=1$ to 8 to produce a polymer

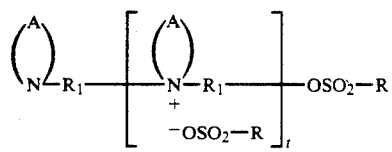

$$\left(\begin{array}{c}A\\ \end{array}\right)_{N-R_1} \left[\begin{array}{c}\left(\begin{array}{c}A\\ \end{array}\right)_{N^+-R_1}\\ ^-OSO_2-R\end{array}\right]_t OSO_2-R \qquad (V)$$

having antimicrobial properties.

2. Composition comprising polymer produced by the process of claim 3 having utility as an antimicrobial agent.

3. Composition according to claim 2 wherein $R_1 = (CH_2)_m$ in which $m = 11$ or 12.

4. Composition according to claim 2 wherein $R_1 = (CH_2CH_2-O)_n-CH_2CH_2$ in which $n = 3$ or 4.

5. Composition according to claim 2 wherein $R_1 = (CH_2CH_2CH_2-O)_n-CH_2CH_2CH_2$ in which $n = 2$ or 3.

6. Composition according to claim 2 wherein m is about 10 to 16.

7. Composition according to claim 2 wherein n is about 2 to 5.

8. Composition according to claim 2 wherein $A = (CH_2)_p$ wherein $p = 4$, or 5 or 6.

9. Composition according to claim 2 wherein R is selected from the group consisting of p-toluene, phenyl, p-toluene, p-chlorophenyl, p-nitrophenyl, and methyl.

10. Process of inhibiting the growth of undesired fungi, bacteria, or algae comprising introducing composition according to claim 2 at a locus.

11. Process of controlling plant pathogenic microbes with low toxicity to said plant comprising applying a composition of claim 2 to plant which is subject to pathogenic microbes.

12. Process of claim 10 wherein the plant pathogen being controlled is selected from the group consisting of genus xanthomonas.

13. Process of controlling virus, bacteria, fungi or algae at a locus comprising applying a composition according to claim 2 to said locus.

14. Topical spray for controlling undesirable bacterial or fungal infection in a human or animal comprising a composition according to claim 2 further comprising an adjuvant.

15. Topical spray according to claim 14 wherein said adjuvant is selected from the group consisting of EDTA and sodium dodecyl alcohol.

* * * * *

UNITED STATES PATENT AND TRADEMARK OFFICE
CERTIFICATE OF CORRECTION

PATENT NO. : 5,149,524
DATED : September 22, 1992
INVENTOR(S) : SE Sherba, RJ Mehta, MM Bowers-Daines, ACT Hsu It is certified that error appears in the above-identified patent and that said Letters Patent is hereby corrected as shown below:

Col. 16, line 2, "claim 3" should read --claim 1--

Signed and Sealed this

Twelfth Day of July, 1994

Attest:

Attesting Officer

BRUCE LEHMAN

Commissioner of Patents and Trademarks